United States Patent [19]

Kruse et al.

[11] 4,369,316
[45] Jan. 18, 1983

[54] 3,1 BENZOXAZINE 2,4-DIONE

[75] Inventors: Walter M. Kruse, Wilmington, Del.; John F. Stephen, West Chester, Pa.

[73] Assignee: ICI Americas Inc., Wilmington, Del.

[21] Appl. No.: 314,178

[22] Filed: Oct. 23, 1981

Related U.S. Application Data

[62] Division of Ser. No. 250,205, Apr. 4, 1981, Pat. No. 4,314,078.

[51] Int. Cl.³ .......................................... C07D 265/26
[52] U.S. Cl. ..................................................... 544/94
[58] Field of Search .......................................... 544/94

[56] References Cited

U.S. PATENT DOCUMENTS 3,513,156  5/1970  Speakman ............................. 544/94
4,306,074 12/1981  Tonne et al. .......................... 544/94

Primary Examiner—Robert W. Ramsuer
Attorney, Agent, or Firm—John M. Sheehan; David J. Levy

[57] ABSTRACT

Preparation of a compound of the following formula (I):

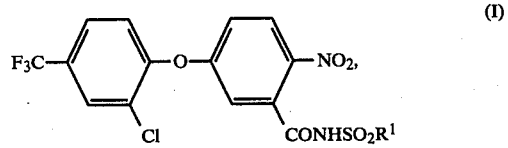

wherein $R^1$ is alkyl of 1 to 12 carbons, from the compound of the following formula (II):

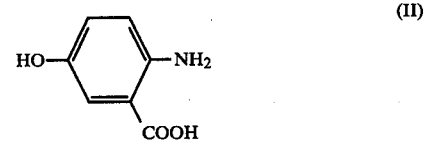

by the steps of coupling (II) with 3,4-dichlorobenzotrifluoride; reacting the —NH$_2$ and COOH groups with a COX$_2$ compound, X being a leaving group, to produce a heterocycle; opening the heterocycle with an alkanesulphonamide; and oxidizing the resultant —NH$_2$ group to an —NO$_2$ to yield a compound of formula (I). Novel intermediates are also described. Compounds of formula (I) are useful as selective pre- and post-emergent herbicides.

1 Claim, No Drawings

3,1 BENZOXAZINE 2,4-DIONE

This is a division of application Ser. No. 250,205, filed on Apr. 4, 1981, now U.S. Pat. No. 4,314,078.

SUMMARY OF THE INVENTION

The invention comprises the preparation of a compound of the following formula (I):

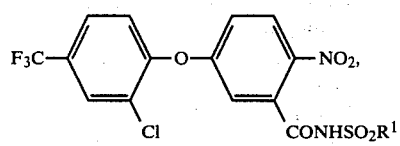

wherein $R^1$ is alkyl of 1 to 12 carbons, from the compound of the following formula (II):

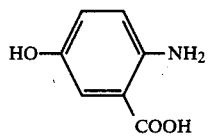

by the steps of coupling (II) with 3,4-dichlorobenzotrifluoride; reacting the —$NH_2$ and COOH groups with an acylating agent to produce a heterocycle; opening the heterocycle with an alkane-sulphonamide; and oxidizing the resultant —$NH_2$ group to an —$NO_2$ to yield a compound of formula (I). Additionally, novel intermediates used in the process are described.

BACKGROUND OF THE INVENTION

Compounds of the following formula (I) are useful as selective herbicides to kill undesirable plant growth among crops such as cotton, soy beans, peas, corn, wheat and rice:

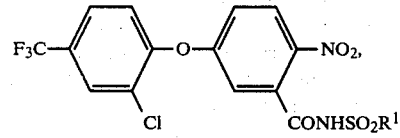

wherein $R^1$ is an alkyl group of 1 to 12 carbons, as disclosed in European Patent Application No. 79300098.5 published Aug. 8, 1979 as publication No. 3416. The compounds of formula (I) are useful both as pre- and post-emergence herbicides when applied at a rate of 0.1 to 5.0 kilograms per hectare.

Processes for the synthesis of compounds of formula (I) are known as seen by a reading of European Patent publication No. 3416. However, many of such processes are disadvantageous from a commercial standpoint in view of the need for nitrating a compound of a formula such as:

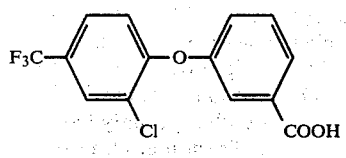

It is an object of the present invention to provide a process for the preparation of compounds of the formula (I) using 2-amino-5-hydroxybenzoic acid or, considering steps leading to 2-amino-5-hydroxybenzoic acid, ortho-nitrobenzoic acid as the starting material. The process of the invention has the advantage of utilizing a starting material with a nitrogen in place at the desired position for the nitro group of the compounds of formula (I). The method of the invention thus is in contrast to known or obvious methods for the synthesis of compounds of formula (I) which require nitrogen substitution on the ring as one of the final steps. This introduction in the prior art of a nitrogen atom on an aromatic ring may be disadvantageous in view of nitrogen atom additions at other than the desired position para to the phenoxy substituent.

DETAILED DESCRIPTION OF THE INVENTION

The following is a scheme of the synthetic pathways described herein for the process of the present invention:

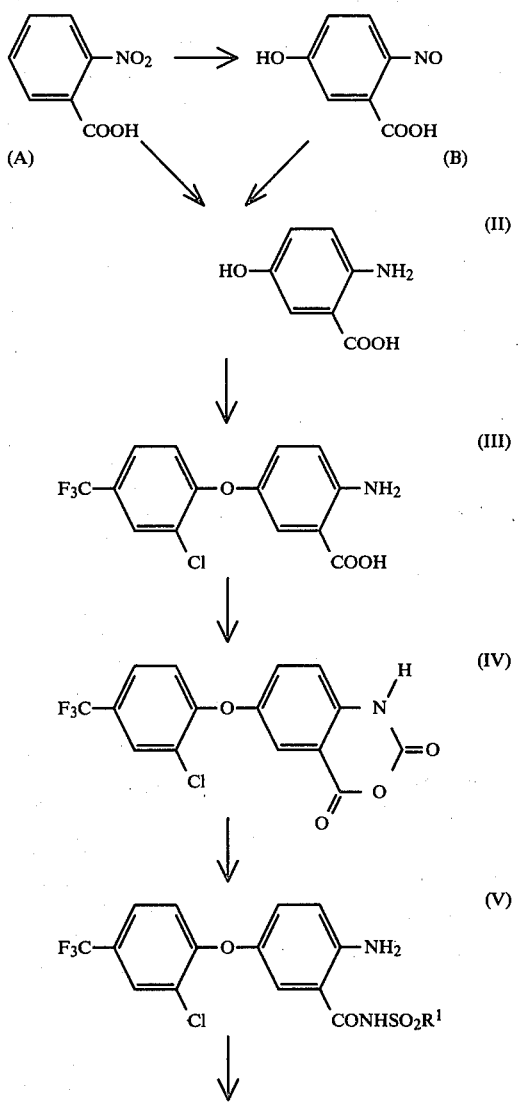

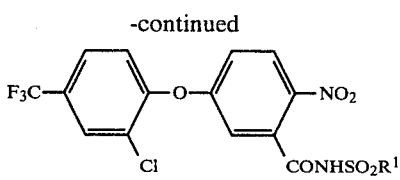

wherein R¹ is alkyl of about 1 to 12 carbons.

Compound (II) is 2-amino-5-hydroxybenzoic acid and is described in Beilsteins Handbuch, XIV, Zweites Ergänzungswerk, page 357 (1951) as 6-amino-3-oxybenzoic acid or 5-oxy-anthranilic acid.

The reaction of compound (II) to produce compound (III) involves coupling of compound (II) which has two nucleophilic moieties, i.e. the HO— and —NH₂ groups, with 3,4-dichlorobenzotrifluoride. A significant aspect of the present invention is the coupling reaction from compound (II) to (III) since it has been found that coupling via the phenolic HO— group, rather than the anilinic —NH₂ group, is the predominant route. Coupling of compound (II) with 3,4-dichlorobenzotrifluoride is preferably done at atmospheric pressure; at about 100° C. to 200° C., preferably about 130° to 175° C.; at a pH of about 7 to 10, preferably about 9 as adjusted by an alkali or alkaline metal carbonate which can be accomplished by using a 30% to 100% molar excess of carbonate based on compound (II); in a dipolar aprotic solvent such as dimethyl sulfoxide, N-methylpyrrolidinone, N,N-dimethylformamide, N,N-dimethylacetamide or sulfolane; a molar ratio of compound (II):3,4-dichloro-benzotrifluoride of about 1:1 to 2:1, preferably about 1.1:1; and for a period of about 15 to 24 hours.

The acylation reaction of compound (III) to produce compound (IV), which is an isatoic anhydride derivative, may be accomplished with an acylation reagent capable of supplying a carbonyl in a manner similar to that used for synthesizing isatoic anhydride itself from anthranilic acid as described by G. M. Coppola in Synthesis, page 505 (1980). Thus, reaction of compound (III) with an acylating agent of the formula COX¹X², wherein X¹ and X² are leaving groups such as COCl₃, OCH₂CH₃ or chlorine, yields the isatoic anhydride derivative (IV). Compound (IV) is a stable, easily handled material which readily separates from solution. The reaction of compound (III) to produce compound (IV) may be carried out in water or an organic solvent such as benzene, toluene, ethyl acetate or acetic acid at temperatures up to reflux although lower temperatures may be sufficient. Preferably, the acylation agent is phosgene.

The reaction of compound (IV) to produce the sulphonamide of formula (V) involves a ring opening and will take place under basic conditions with an excess of an alkanesulphonamide of the formula H₂NSO₂R¹, wherein R¹ is alkyl of about 1 to 12 carbons, preferably 1 to 4 carbons, such as methanesulphonamide. The reaction may be carried out at atmospheric pressure; at about 80° to 150° C., preferably about 100° to 120° C.; in a dipolar aprotic solvent such as N-methylpyrrolidinone, N,N-dimethylformamide, N,N-dimethylacetamide or sulfolane; at a molar ratio of the alkanesulphonamide:compound (IV) of about 1:1 to 5:1, preferably about 2:1; and with the addition of at least 1 mole, per mole of compound (IV), of an alkali metal hydroxide to provide the reactive anion of the alkanesulphonamide.

The last step of the process of the invention involves oxidizing compound (V) with an oxidation agent to yield a 5-(2-chloro-4-trifluoromethylphenoxy)-2-nitro-N-alkanesulphonyl benzamide of formula (I). The oxidation agent may be a peracid such as peracetic acid, perphthalic acid, permaleic acid or hydrogen peroxide may be used. Reaction conditions will depend on the particular agent but in general, the oxidation may be carried out at atmospheric pressure; at a temperature from about 25° to 90° C., preferably about 75° C.; in the presence of a mineral acid catalyst such as sulfuric or nitric acid; in a solvent such as acetic acid or a mixture of acetic acid and a chlorinated solvent such as methylene dichloride, ethylene dichloride or chlorobenzene; in a molar ratio of oxidation agent:compound of formula (V) of about 2:1 to 8:1, preferably about 5:1; and for a period of about 5 to 20 hours.

Although the starting material of formula (II) for the process of the invention is a known compound, a further feature of the present invention is the total process for the preparation of a compound of formula (I) by starting with ortho-nitrobenzoic acid of the formula (A):

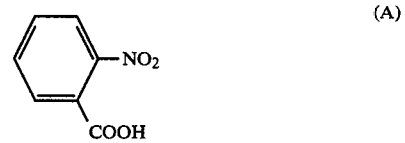

and proceeding to formula (II).

From ortho-nitrobenzoic acid of formula (A), the synthesis may either proceed directly to formula (II) by use of a Bamberger-type reaction or through a nitroso intermediate of the following formula (B):

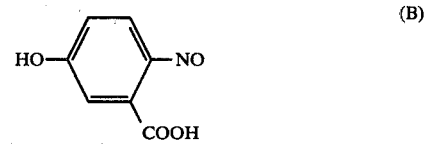

by reaction of (A) with a strongly basic hydroxide and subsequent reduction of (B) to yield (II).

In the direct preparation of (II) from (A), catalytic hydrogenation is used in an acidic medium to cause a Bamberger-type reaction in a manner similar to that described by E. Bamberger in Annalen der Chemie 424 page 233 (1921) or E. D. Hughes and C. K. Ingold in Quarterly Reviews 6, page 34 (1952) at page 45. The hydrogenation proceeds at a hydrogen pressure of about 3 to 30, preferably about 5 to 10, pounds per square inch; a temperature of about 80° to 140° C., preferably about 100° C.; a pH from below 1 to about 2, preferably about 1; using an aqueous mineral acid solvent such as sulfuric acid, e.g. 10% of 12 molar sulfuric acid in water; and in this presence of a hydrogenation catalyst such as palladium or platinum, for example 5% palladium on carbon.

Alternatively, (II) may be prepared from (A) through compound (B). This stepwise preparation of compound (II) has the advantage of avoiding certain side reactions such as the cyclization of the intermediate which has a hydroxylamine moiety in the place of the —NO₂ of compound (A) as might occur in the direct reaction of (A) to (II). The reaction of compound (A) to yield (B) can be carried out with a strongly basic hydroxide, e.g. as described by A. Treston et al. in the Journal of the Chemical Society, Chem. Comm., page 394 (1980). In this article, 2-nitrobenzoic acid is reacted with 15.8 molar potassium hydroxide at 60° C. under nitrogen for 20 hours. The nitroso compound (B) may then be reduced by catalytic hydrogenation under conditions described by P. N. Rylander in "Catalytic Hydrogenation over Platinum Metals", Academic Press, New York (1967) at page 164. For example, the catalyst may be a noble metal such as palladium or platinum or Raney nickel using a solvent such as an alcohol or water.

Also within the scope of the present invention are novel intermediates used in the process of the present invention. One of the novel intermediate compounds is that of the formula (IV).

In the following Examples, the following abbreviations are used: g (grams); ml (milliliters); N (normal); mm (millimeters); C. (centigrade); m.p. (melting point); psi (pounds per square inch).

EXAMPLE I

Preparation of 2-amino-5-hydroxybenzoic acid (II) from (A)

4.5 g of ortho-nitrobenzoic acid are added to 100 ml of a 10% by weight of 10 N sulfuric acid in water solution. To the solution is then added 0.5 g of 5% platinum-on-carbon hydrogenation catalyst. The slurry is then stirred and hydrogenated at a hydrogen pressure of 20 psi about 80° to 100° C. for a period of about 20 hours. After hydrogenation, the catalyst is removed by filtration and the filtrate evaporated in vacuo to give a mixture containing about 30% by weight of the desired product of formula (II) which may be purified by chromatography, for example column chromatography with silica gel.

EXAMPLE II

Preparation of 2-amino-5-hydroxybenzoic acid (II) from (A) through (B)

To a solution of 49 g of potassium hydroxide in 35.5 ml of water is added 4 g of ortho nitrobenzoic acid and the resultant slurry is placed in a pressure bottle. The bottle is then placed in a thermostatically-controlled bath at 60° C. for 20 hours. A deep red supernatant liquid and a yellow precipitate results which is separated by filtration. The precipitate contains the dipotassium salt of 2-nitroso-5-hydroxybenzoic acid of formula (B).

A solution of 4 g of the above-described yellow precipitate and 50 ml of water is prepared and 0.5 g of 5% palladium on carbon is added. The resultant slurry is added to a pressure bottle which is then capped and evacuated. To the bottle hydrogen is then introduced which is maintained at a pressure of 30 psi and it is kept in an oil bath at 100° C. for 8 hours. Thin layer chromatography of the product against an authentic sample indicates a major product to be 5-hydroxyanthranilic acid of the formula (II) which may be isolated by filtering the reaction product slurry to recover catalyst and chromatographically purifying it from anthranilic acid with silica gel.

EXAMPLE III

Coupling reaction to yield compound (III)

A slurry of 153.1 g of 2-amino-5-hydroxybenzoic acid, 221.5 g of 3,4-dichlorobenzotrifluoride, 150.6 g of finely ground potassium carbonate and 1800 ml of N,N-dimethylacetamide is prepared and stirred under $N_2$ at about 135° C. for about 17 hours. After cooling to room temperature, the mixture is neutralized to a pH of 6 to 7 by the addition of an aqueous ethanolic solution of hydrochloric acid, equivalent to about 1.2 moles of HCl, filtered and vacuum evaporated at about 60° to 80° C. to yield the compound of formula (III).

EXAMPLE IV

Acylation to yield compound (IV)

Liquid phosgene in an amount of 108.9 g is added to a stirred solution of 331.6 g of the diphenyl ether derivative product of Example (III) in 3000 ml of toluene. The temperature is raised to and maintained at about 40°–45° C. for about 2 hours. Upon cooling to room temperature, the isatoic anhydride derivative (IV) is precipitated out of solution as in an amount of 321.9 g and is collected by filtration, m.p. 240° C. (decompose).

EXAMPLE V

Preparation of compound (V), $R^1$=methyl

The potassium salt of methanesulphonamide is prepared by firstly stirring 1.43 g of methanesulphonamide in 100 ml of toluene under nitrogen. 0.74 g of potassium hydroxide pellets are then added, and the mixture is heated to reflux with removal of water as a water-toluene azeotrope. After complete water removal, the toluene is distilled off with simultaneous addition of 100 ml of dimethyl formamide (DMF), thereby producing a suspension of the potassium salt of methanesulphonamide in DMF.

The suspension is then heated to about 100° C. and a solution of 2 g of the isatoic anhydride derivative of formula (IV) product of Example IV in about 50 ml of DMF is added with stirring over one hour. The mixture is then maintained at about 100° C. for 24 hours after which the DMF is removed by distillation. The residue is then purified by chromatography using silica gel and toluene, ethyl acetate or mixtures of isopropanol and methylene chloride as the solvent to yield 2-amino-5-(2-chloro-4-trifluoromethylphenoxy)-N-methane-sulphonyl benzamide having the formula (V) wherein $R^1$ is methyl, m.p. 185°–186° C.

EXAMPLE VI

Oxidation to yield formula (I), $R^1$=methyl

A stirred solution is prepared containing 39.5 g of 2-amino-5-(2-chloro-4-trifluoromethylphenoxy)-N-methanesulphonyl benzamide of the formula (V), $R^1$=methyl, 1380 ml of glacial acetic acid and 1.0 g of concentrated nitric acid at about 40° C. To the solution is added 138 g of a 30% by weight hydrogen peroxide in water solution and the reaction mixture is raised to and maintained at about 70° C. for 20 hours. The solution is then poured slowly into about 3 liters of ice water with precipitation of crude product. After filtration, the product is isolated as a solid, m.p. 175°–183° C., containing 68% of the compound of formula (I), $R^1$=methyl, as determined by high pressure liquid chromatography, thin layer chromatography and its mass spectrum. Recrystallization from aqueous methanol yields the product 5-(2-chloro-4-trifluoromethylphenoxy)-2-nitro-N-methanesulphonyl benzamide, m.p. 216°–218° C.

What is claimed is:

1. The compound of the following formula (IV):

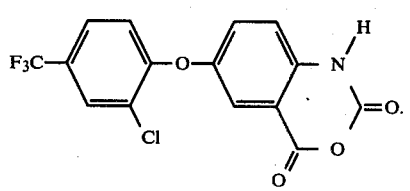
(IV)
* * * * *